United States Patent [19]

Andersen et al.

[11] Patent Number: 4,715,881

[45] Date of Patent: Dec. 29, 1987

[54] CONTROL OF EASTERN BLACK NIGHTSHADE WITH A FUNGAL PATHOGEN

[75] Inventors: Robert N. Andersen, St. Paul, Minn.; Harrell L. Walker, Ruston, La.

[73] Assignee: The United States of America as represented by the Secretary of Agriculture, Washington, D.C.

[21] Appl. No.: 738,707

[22] Filed: May 29, 1985

[51] Int. Cl.$^4$ ............... C12N 1/14; C12R 1/645; A01N 63/00; A01H 1/00
[52] U.S. Cl. ................................. 71/79; 71/65; 435/254; 435/911; 424/93; 47/58
[58] Field of Search ............... 71/65, 79; 424/93; 435/911, 254; 47/58

[56] References Cited

U.S. PATENT DOCUMENTS 3,849,104  11/1974  Daniel et al. ............... 71/65
3,999,973  12/1976  Templeton ................. 71/79
4,419,120  12/1983  Walker ..................... 71/79

OTHER PUBLICATIONS

Agriculture Handbook No. 165, U.S.D.A. Index of Plant Diseases in the United States, 1960, p. 456.
Anderson, R. N. and H. L. Walker, 1985, *Colletotrichum coccodes*: A Pathogen of Eastern Black Nightshade (*Solanum ptycanthum*), Weed Science, 33:902–905.
J. T. Daniel et al., "Biological Control of Northern Jointvetch in Rice with an Endemic Fungal Disease," Weed Sci., 21(4): 303–307 (Jul. 1973).
A. R. Gotlief et al., "*Colletotrichum coccodes*, a Pathogen of Velvetleaf (*Abutilon theophrasti*): A Potential Mycoherbicide," Abstr. #174, 1984 Meeting of the Weed Science Society of America, Miami, FL, Feb. 8–10, 1984.

*Primary Examiner*—Thomas G. Wiseman
*Assistant Examiner*—David T. Fox
*Attorney, Agent, or Firm*—M. Howard Silverstein; David G. McConnell; Curtis P. Ribando

[57] ABSTRACT

A strain of *Colletotrichum coccodes* has been discovered which is selectively pathogenic toward eastern black nightshade (*Solanum ptycanthum*). Formulations comprising propagules of the fungal pathogen are useful for biological control of the eastern black nightshade weed, particularly in agricultural fields.

10 Claims, No Drawings

CONTROL OF EASTERN BLACK NIGHTSHADE WITH A FUNGAL PATHOGEN

BACKGROUND OF THE INVENTION

1. Field of the Invention

Eastern black nightshade (*Solanum ptycanthum*) is an economically important weed in much of the midwestern United States. It can cause crop yield reductions by competition, but is more notorious for interfering with harvest and lowering the crop quality. The foliage and berries of eastern black nightshade can foul combines and make harvesting nearly impossible. Moreover, the berries contaminate and stain the crop seeds and initiate mold growth during storage. Several species of weedy nightshades, including the eastern black nightshade, have in the past been generically referred to as "black nightshade" (*Solanum nigrum* L.). In accordance with a recent taxonomic revision, the eastern black nightshade is now designated as a separate species, *Solanum ptycanthum*.

This invention relates to a method of controlling eastern black nightshade by means of infection with a fungal pathogen.

2. Description of the Prior Art

The merits for using pathogens to control weeds in annual crops have been discussed previously for various fungal species. Daniel et al., U.S. Pat. No. 3,849,104 teaches the use of an endemic anthracnose fungus, *Colletotrichum gloeosporioides* forma specialis *aeschynomene*, to control the northern jointvetch weed in rice fields. A related species, *C. malvarum*, has been reported by Templeton in U.S. Pat. No. 3,999,973 as a control for prickly sida (*Sida spinosa* L.) or teaweed, particularly in soybean and cotton fields. *C. malvarum is also pathogenic toward other noncultivated species, including velvetleaf. C. coccodes* has been well documented as a widely distributed pathogen of potato and tomato, as well as 35 other plant species throughout the world. One isolate of *C. coccodes* has been studied as a potential mycoherbicide for velvetleaf by Gotlief et al. [Proc. Weed Sci. Soc. Am. 37: 68 (1984)].

Walker [Weed Sci. 29: 505-507 (1981)] discloses the use of *Alternaria macrospora* as a pathogen against spurred anoda. In Walker, U.S. Pat. No. 4,390,360, *A. cassiae* is disclosed as an effective biological control agent for sicklepod, showy crotalaria, and coffee senna. Finally, Walker teaches in U.S. Pat. No. 4,419,120 that *Fusarium lateritium* is useful in controlling prickly sida, velvetleaf, and spurred anoda.

SUMMARY OF THE INVENTION

We have now discovered a strain of *Colletotrichum coccodes* which is pathogenic toward eastern black nightshade but innocuous toward virtually all crop species for which the nightshade poses agronomic difficulties. This invention is drawn to the use of this fungus as a mycoherbicide for controlling eastern black nightshade and other susceptible species and also to mycoherbicidal compositions comprising *C. coccodes* propagules. In practice, the target plants are inoculated by treating infested fields with the propagule-containing compositions.

In accordance with this discovery, it is an object of this invention to provide a mycoherbicidal alternative to chemical control of eastern black nightshade.

It is also an object of the invention to provide a biological herbicide for eastern black nightshade which is nonpathogenic toward crop species.

Another object of the invention is to provide a fungal pathogen which can be artificially mass-produced and formulated for both preemergence and postemergence weed control.

Other objects and advantages of this invention will become readily apparent from the ensuing description.

DETAILED DESCRIPTION OF THE INVENTION

The fungal organism for use herein is a strain of *C. coccodes* isolated from a field of eastern black nightshade experimental plots near Rosemount, Minnesota. In late summer, following an extended period of abundant rainfall and high humidity, this strain was found to be responsible for a disease epihytotic in the plots. Nearly all the eastern black nightshade plants had been killed, and those remaining were in an unhealthy state.

The taxonomic characteristics of the isolate are typical of the species. The acervuli growing on stems and roots are rounded or elongated, and attain a diameter of approximately 300$\mu$. The acervular tissue occurs both intra- and subepidermal, disrupting the outer epidermal cell walls of the host. Setose sclerotia are common. The spores are cylindrical with obtuse ends, ranging in length from 16 to 24$\mu$ and in diameter from 2.5 to 4.5$\mu$. The spores are hyaline and aseptate and are formed from unicellular hyaline cylindrical phialidic conidiophores. This isolate has been deposited in the Agricultural Research Culture Collection (NRRL) in Peoria, Ill., and has been assigned Accession Number NRRL 15547. For purposes of this invention, any isolate of *C. coccodes* having the identifying characteristics of NRRL 15547 including subcultures thereof would be effective.

The fungal propagules including the spores (conidia) and mycelia can be mass-produced for field inoculations by culturing the *C. coccodes* on half-strength Emerson's yeast-starch agar as described below:

| Emerson's Yeast-Starch Agar | |
|---|---|
| Nutrient | Concentration (g./L.) |
| powdered yeast extract ("Difco") | 2 |
| soluble starch | 7.5 |
| $K_2HPO_4$ | 0.5 |
| $MgSO_4.7H_2O$ | 0.25 |
| distilled water | |

The propagules are preferably incorporated into compositions suitable for field application. They can be omitted with any liquid vehicle or solid carrier such as water, emulsions, clay, vermiculite, $CaCO_3$, corn cob grits, etc. Both the spores and mycelia lend themselves to formulation as liquid sprays and wettable powders for postemergence treatment. They can also be formulated as controlled-release granules for preemergence weed control. Infection is promoted in the presence of free moisture (dew) for a period of at least about 12 hours. At a temperature of 25° C., the optimal moisture period is 16 to 20 hours.

The actual concentration of propagules in the formulated composition is not particularly critical, and is a function of practical considerations such as the properties of the vehicle or carrier, and the method of application. For purposes of formulation and application, an "effective amount" is defined to mean any such quantity of propagules sufficient to infect the target plant and thereby induce the symptoms of the disease described below.

It is understood that application of the mycoherbicide does not require immediate direct contact with the target plant. It may be applied in the locus or vicinity of the plant and rely upon natural environmental conditions for infection. In this manner, the herbicide is effective as a preemergent treatment.

Though current data indicate that *C. coccodes* is a relatively selective pathogen of eastern black nightshade, it is within the compass of this invention to treat other undesirable plant species which prove to be susceptible to this disease. For example, as shown by the data in Example 4, below, other species of nightshade are infected and damaged to varying degrees by *C. coccodes*.

When infecting eastern black nightshade, the organism produces typical anthracnose lesions. These lesions are grey, water-soaked-appearing spots, which later become necrotic spots. The lesions tend to spread and eventually kill the plant. Unlike other strains of *C. coccodes* which are known to be pathogenic toward tomato and potato plants, NRRL 15547 is innocuous toward these species, as well as toward all other major crop species tested, including corn, grain sorghum, rice, soybeans, cotton, eggplant, peppers, and tobacco.

The following examples are intended only to further illustrate the invention and are not intended to limit the scope of the invention which is defined by the claims.

EXAMPLE 1

Pathogen Isolation and Culture

Diseased plants of eastern black nightshade were collected from experimental plots near Rosemount, Minn. Infected plant pieces were placed on moist filter paper in plastic petri dishes for several days in a growth chamber to promote sporulation of the pathogen. Then, pieces of plant tissue were placed on the leaves of greenhouse-grown seedlings of eastern black nightshade, accession A37. Pots of seedlings were enclosed in plastic bags containing wet paper towels and placed in shade under a greenhouse bench. After 48 hours, the bags were removed, pots were placed on greenhouse benches, and seedlings were observed for disease development. Diseased seedlings were sent, as fresh shoots pressed between paper towels, to Stoneville, Miss.

*Colletotrichum coccodes* was isolated from a diseased seedling at Stoneville on potato dextrose agar (PDA) ("Difco") supplemented with streptomycin sulfate (125 mg./L.) and chloramphenicol (75 mg./L.). The fungus was cultured in petri dishes of growth media incubated at 25° C. with 12-hour photoperiods. Light was provided by two 15-watt cool-white fluorescent lamps that were suspended 45 cm. above the cultures. The pathogen produced sclerotia on PDA, but did not sporulate readily on this medium. Abundant conidia were produced on half-strength Emerson's yeast-starch agar, and these conidia were used as inoculum for greenhouse tests. Conidia were also produced in submerged liquid cultures, using the corn meal-soyflour-sucrose medium and the modified Richard's medium described below, but sporulation was inconsistent.

| Corn Meal-Soyflour-Sucrose Medium[1] | |
|---|---|
| Nutrient | Concentration (g./L.) |
| corn meal | 15 |
| soybean flour | 15 |
| sucrose | 30 |
| CaCO$_3$ | 3 |

[1]Nutrients were dissolved or dispersed in distilled water and the medium pH was approximately 7.0.

| Modified Richard's Medium[1] | |
|---|---|
| Nutrient | Concentration (g./L.) |
| sucrose | 50 |
| KNO$_3$ | 10 |
| KH$_2$PO$_4$ | 5 |
| MgSO$_4$.7H$_2$O | 2.5 |
| FeCl$_3$ | 0.02 |
| "V-8" juice | 150 ml./L. |

[1]Nutrients were dissolved in distilled water and the solution was adjusted to pH 6 with 50% (w/v) NaOH.

EXAMPLE 2

Seedlings for host range tests at Stoneville, Miss., were greenhouse-grown in 5.5-cm. square peat pots containing a commercial blend of peat, pine bark, and perlite with one seedling per pot. Aqueous suspensions were prepared comprising conidia of the eastern black nightshade isolate of *C. coccodes* produced by culture on the half-strength Emerson's yeast-starch agar in 0.05% (w/v) oxysorbic (20 POE) polyoxyethylene sorbitan monooleate surfactant ("Tween 80") at a concentration of $1 \times 10^6$ conidia/ml. The seedlings were inoculated by wetting the foliage with the suspension in the third- to fourth-leaf stage. Immediately following inoculation, the plants were placed in dark dew-chambers (25° C.) for 24 hours, then moved to greenhouse benches and evaluated for disease symptoms 14 days after inoculation. Susceptible plants displayed anthracnose symptoms (necrotic lesions) usually within 3 days following inoculation.

A randomized complete block design was used with three replicates consisting of 12 plants of each species per replicate. The experiment was conducted twice. The results are reported in Table I, below.

EXAMPLE 3

The procedure of Example 2 was repeated except that the seedlings were inoculated by injecting approximately 20 μL. of the conidial suspension into the stems.

A randomized complete block design was used with three replicates consisting of 12 plants of each species per replicate. The experiment was conducted twice. The results are reported in Table II, below.

EXAMPLE 4

Tests were conducted at St. Paul, Minn., to determine the reaction of weeds of the Solanaceae to the pathogen. Seedlings were started in peat pellets in the greenhouse, then transplanted to 250-ml. plastic cups of potting soil with one seedling per cup. The plants were inoculated by wetting the foliage with a conidial suspension containing 0.05% (w/v) of "Tween 80" and having approximately $1 \times 10^6$ conidia/ml. Immediately after inoculation, plants were placed in a dark dew-chamber on a greenhouse bench for 24 hours before being returned to the greenhouse bench. Temperatures in the greenhouse were 22±4° C. and humidity was 30 to 50%. Natural light was supplemented with light from fluorescent tubes to give a 16-hour photoperiod.

TABLE I

Reaction of Various Plant Species to the Foliar Spray of *Colletotrichum coccodes* Pathogen

| Species | Disease Rating[a] |
|---|---|
| Gramineae | |
| Corn (*Zea mays* L. 'XL 394') | NS |
| Grain sorghum [*Sorghum bicolor* (L.) Moench 'Texas C 424'] | NS |
| Rice (*Oryza sativa* L. 'Starbonnet') | NS |
| Leguminosae | |
| Soybean [*Glycine max* (L.) Merr. 'Centennial'] | NS |
| Malvaceae | |
| Velvetleaf (*Abutilon theophrasti* Medic.) | NS |
| Cotton (*Gossypium hirsutum* L. 'DPL 61') | NS |
| Solanaceae | |
| Eastern black nightshade (*Solanum ptycanthum* Dun.) | S |
| Eggplant (*Solanum melongena* L. 'Black Beauty') | NS |
| Pepper (*Capsicum annuum* L.) | NS |
| Petunia (*Petunia hybrida* Vilm. 'Confetti multiflora') | NS |
| Potato (*Solanum tuberosum* L. 'Red LaSoda') | NS |
| Tobacco (*Nicotiana tabacum* L.) | |
| 'NC 95' | NS |
| 'NC 2326' | NS |
| Tomato (*Lycopersicon esculentum* Mill.) | |
| 'Rutgers' | NS |
| 'Marglobe' | NS |
| 'Better Boy' | NS |
| 'Patio' | NS |

[a]Rating scale: NS = No disease symptoms, S = susceptible.

TABLE II

Reaction of Various Plant Species to Injected *Colletotrichum coccodes* Pathogen

| Species | Disease Rating[a] |
|---|---|
| Malvaceae | |
| Velvetleaf (*Abutilon theophrasti* Medic.) | NS |
| Solanaceae | |
| Eastern black nightshade (*Solanum ptycanthum* Dun.) | S |
| Potato (*Solanum tuberosum* L. 'Red LaSoda') | NS |
| Tomato (*Lycopersicon esculentum* Mill.) | |
| 'Rutgers' | NS |
| 'Marglobe' | NS |
| 'Better Boy' | NS |
| 'Patio' | NS |

[a]Rating scale: NS = No disease symptoms, S = susceptible.

Two experiments were conducted. Eastern black nightshade, accession A37, was included in both experiments. For each species or accession of weeds, 15 plants were inoculated and five plants, wetted only with water, served as controls. The experiments were in completely randomized designs with 15 single-plant replicates of each species or accession. Visual ratings of disease injury (0=no effect, 5=dead) were made 9 days after inoculation. The results are reported in Table III, below.

EXAMPLE 5

To study the effect of dew period duration on disease development, seedlings of eastern black nightshade in the third- to fourth-leaf stage were inoculated by wetting the foliage with conidial suspensions of the pathogen ($1 \times 10^6$ conidia/ml.) and placed in dark, dew-chambers at 25° C. After 0, 4, 8, 12, 16, and 24 hours, groups of 12 inoculated and 12 control plants were removed from the dew-chambers, placed on greenhouse benches, and evaluated for disease development 14 days after inoculation. In general, maximum disease development (95–100% of plants killed) occurred for the dew periods of 16 hours or longer, with 40% of the plants being killed after a dew period of 12 hours.

It is understood that the foregoing detailed description is given merely by way of illustration and that modification and variations may be made therein without departing from the spirit and scope of the invention.

TABLE III

Reaction of Weeds of the Solanaceae to Foliar Spray of the *Colletotrichum coccodes*

| Species | Accession[a] | True leaves when treated (no.) | Injury rating[b] (0–5) |
|---|---|---|---|
| First experiment | | | |
| Eastern black nightshade (*S. ptycanthum* Dun.) | A37 | 4 | 4.8 |
| Eastern black nightshade (*S. ptycanthum* Dun.) | A23 | 4 | 4.4 |
| No common name (*S. interius* Rydb.) | A14 | 4 | 3.5 |
| Hairy nightshade (*S. sarrachoides* Sendtner # SOLSA) | A32 | 5 | 2.5 |
| Hairy nightshade (*S. sarrachoides* Sendtner) | A29 | 5 | 2.2 |
| American nightshade (*S. americanum* Mill. # SOLAM) | A59 | 4 | 2.3 |
| Black nightshade (*S. nigrum* L. subsp. nigrum) | A3 | 4 | 1.7 |
| Black nightshade [*S. nigrum* L. subsp. schultessi (Opiz) Wessely] | ND3 | 3 | 2.4 |
| Second Experiment | | | |
| Eastern black nightshade (*S. ptycanthum* Dun.) | A37 | 4 | 4.9 |
| Cutleaf nightshade (*S. triflorum* Nutt. # SOLTR) | — | 4 | 1.9 |
| Jimsonweed (*Datura stramonium* L. # DATST) | — | 3 | 1.1 |
| Buffalobur (*S. rostratum* Dun. # SOLCU) | — | 3 | 0.6 |

[a]Accession numbers identify strains of weeds maintained by Robert N. Andersen in Minnesota.
[b]0 = No effect, 5 = Dead; LSD (0.05) = 0.1.

We claim:

1. A method for controlling plants of the genus Solanum comprising inoculating a susceptible plant of the genus Solanum with an effective amount of a strain of the fungus *Colletotrichum coccoides* having all the identifying characteristics of NRRL 15547.

2. A method for controlling plants of the genus Solanum comprising applying infective propagules of a strain of the fungus *Colletotrichum coccoides* having all the identifying characteristics of NRRL 15547 to a susceptible plant of the genus Solanum or the leaves thereof in an amount effective to infect the plant.

3. A composition for controlling plants of the genus Solanum comprising infective propagules of a strain of the fungus *Colletotrichum coccoides* having all the identifying characteristics of NRRL 15547 and a suitable agricultural carrier therefor.

4. A method as described in claim 1 wherein said plant is eastern black nightshade.

5. A method as described in claim 4 wherein said plant is eastern black nightshade.

6. A method as described in claim 4 wherein said infective propagules are applied in combination with a suitable agricultural carrier.

7. A method as described in claim 6 wherein said infective propagules are spores.

8. A method as described in claim 4 wherein said infective propagules are applied as a spray formulation or wettable powder.

9. A method as described in claim 4 wherein said infective propagules are applied as a granular formulation.

10. A composition as described in claim 3 wherein said infective propagules are spores.

* * * * *

UNITED STATES PATENT AND TRADEMARK OFFICE
CERTIFICATE OF CORRECTION

PATENT NO. : 4,715,881
DATED : December 29, 1987
INVENTOR(S) : Robert N. Andersen and Harrell L. Walker It is certified that error appears in the above—identified patent and that said Letters Patent is hereby corrected as shown below:

Column 2, line 18, delete "epihytotic" and insert -- epiphytotic -- ;
Column 2, line 53, delete "omitted" and insert -- combined -- .
Claim 1, lines 1 and 3, both occurrences of "Solanum" should be italicized.
Claim 2, lines 1 and 5, both occurrences of "Solanum" should be italicized.
Claim 3, line 2, "Solanum" should be italicized.
Claims 5, 6, 8, 9, delete "4" and insert -- 2 -- .

Signed and Sealed this

Second Day of January, 1990

Attest:

JEFFREY M. SAMUELS

Attesting Officer     Acting Commissioner of Patents and Trademarks